United States Patent [19]

Pollhammer et al.

[11] Patent Number: 5,543,560
[45] Date of Patent: Aug. 6, 1996

[54] HYDROGENOLYTIC REDUCTION OF PEROXIDIC OZONOLYSIS PRODUCTS

[75] Inventors: Stefan Pollhammer; Josef Scaller, both of Linz; Willibald Winetzhammer, Steinhaus, all of Austria

[73] Assignee: Chemie Linz Gesellschaft m.b.H., Linz, Austria

[21] Appl. No.: 208,673

[22] Filed: Mar. 11, 1994

[30] Foreign Application Priority Data

Mar. 12, 1993 [AT] Austria ..................................... 484/93

[51] Int. Cl.$^6$ ............................. C07C 67/03; C07C 41/00; C07C 205/00
[52] U.S. Cl. ..................... 560/234; 568/423; 568/424; 568/430; 568/469; 568/672
[58] Field of Search ..................... 568/423, 430, 568/424, 469, 672; 560/234

[56] References Cited

U.S. PATENT DOCUMENTS

| | | | |
|---|---|---|---|
| 4,513,149 | 4/1985 | Gray et al. | 564/449 |
| 4,607,126 | 8/1986 | Sajtos | 568/385 |
| 4,769,464 | 9/1988 | Sajtos | 546/314 |
| 5,015,760 | 5/1991 | Sajtos | 560/186 |
| 5,063,194 | 11/1991 | Broecker et al. | 502/314 |

FOREIGN PATENT DOCUMENTS 362000 4/1970 U.S.S.R. ..................... C07C 47/12

OTHER PUBLICATIONS

E. Müller, Methoden der Organischen Chemie, vol. VII, Part 1, 4th Ed., pp. 336–337, Georg Thieme Verlag, Stuttgart, (1954).

*Primary Examiner*—Jose' G. Dees
*Assistant Examiner*—Rosalynd A. Williams
*Attorney, Agent, or Firm*—Wenderoth, Lind & Ponack

[57] ABSTRACT

A method for the hydrogenolytic reduction of peroxidic ozonolysis products to the corresponding carbonyl compounds in the presence of an inert organic diluting agent and in the presence of a monolith catalyst at hydrogen pressures of 0.01 to 2.0 MPa and at temperatures of –10° to 150° C., and a device for the catalytic hydrogenolysis of chemical compounds which yield uniform, new products by means of hydrogenolysis with hydrogen.

7 Claims, 1 Drawing Sheet

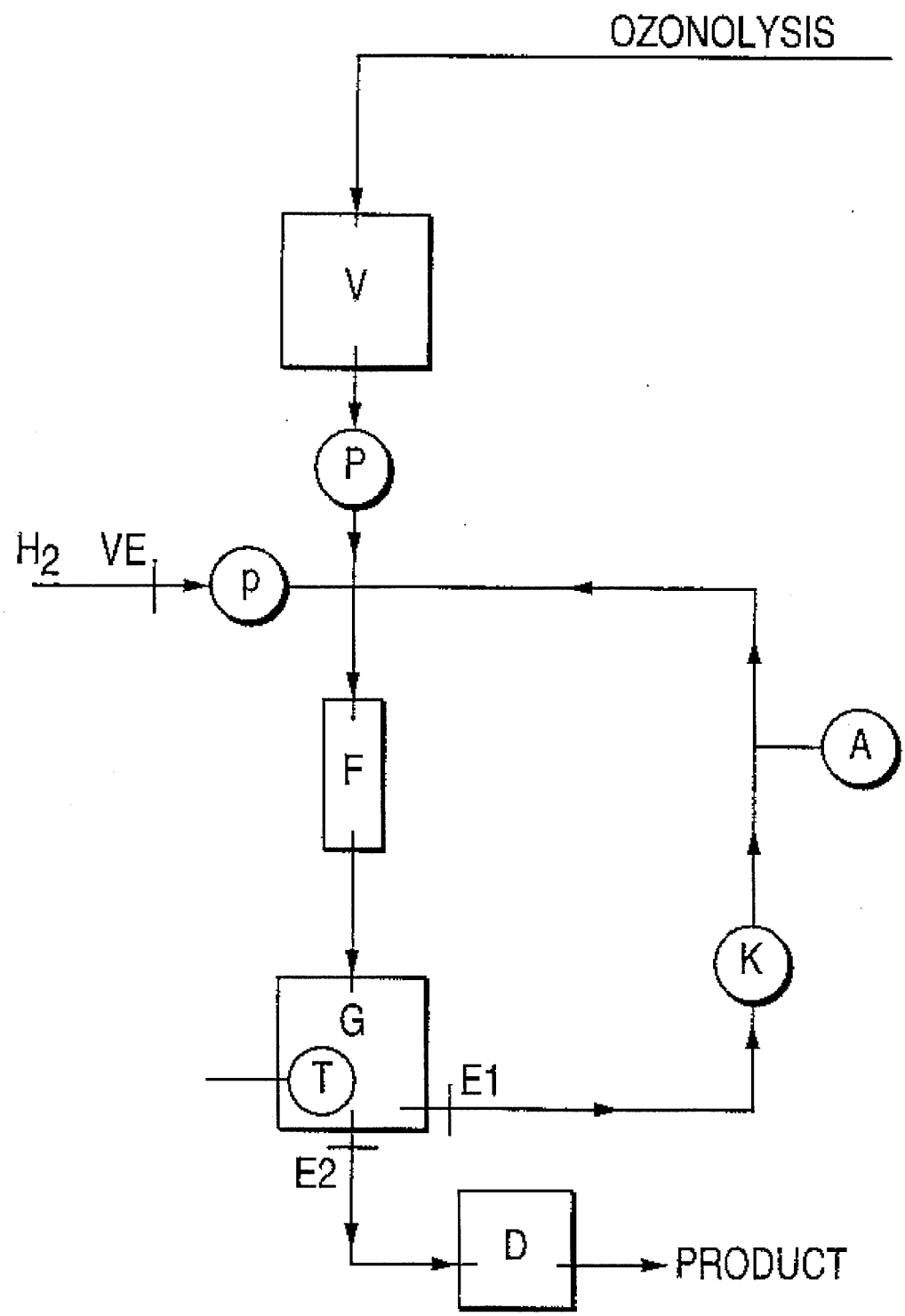

ium chloride, dichloroethane, chlorobenzenes, carboxylic acid esters such as methyl, ethyl or butyl-acetate, ethers such as diethyl ether, diisopropyl ether, tetrahydrofuran, ketones such as acetone or methylbutyl ketone, alcohols such as methanol, ethanol or isopropanol are to be understood. When alcohols are employed as diluting agents, not only aldehydes or ketones which correspond to the olefins can be formed as products, but also their hemiacetals, acetals, or their ketone acetals, whereby acetalation or ketalation is primarily dependent on the pH value conditions.

HYDROGENOLYTIC REDUCTION OF PEROXIDIC OZONOLYSIS PRODUCTS

The ozonolysis of olefins generates in an environmentally friendly way carbonyl compounds such as aldehydes or ketones or, depending on the preparation conditions, their hemiacetals, acetals or ketone acetals, which are valuable parent materials in preparative organic chemistry. As is known, peroxides which can be converted to the desired products only after reduction are also formed during ozonolysis. Methods for the production of carbonyl compounds and their acetals, hemiacetals or ketone acetals on a commercial scale by means of ozonolysis or reduction are described in U.S. Pat. No. 4,607,126 and U.S. Pat. No. 4,769,464. According to the disclosures in these two patent claims, compounds containing olefin double bonds are converted in a low, aliphatic alcohol at temperatures of −80° C. to 20° C. with the equivalent amount of ozone, after which the peroxidic reaction solution is fed into a suspension of a hydrogenation catalyst while adding hydrogen in such a way that a peroxide concentration of 0.1 mole/l is not exceeded in the reaction mixture. Since acid by-products which would toxify and quickly deactivate the catalyst are formed when the reaction is conducted in this way, the reaction mixture's pH value must be controlled by adding a base.

Unexpectedly, it was found that virtually no by-products are formed during the method described above when a monolith catalyst is used instead of the conventional catalyst suspension, even when the same catalyst basic substance, e.g. palladium or platinum is employed. Furthermore, during comparative trials, it was discovered that the employment of a monolith catalyst produces higher yields and purer products, whereby the catalyst remains highly active over a long period of time.

The object of the invention is therefore a method for the hydrogenolytic reduction of peroxidic ozonolysis products to the corresponding carbonyl compounds in an organic diluting agent which is inert under the reaction conditions in the presence of a catalyst at a hydrogen pressure of 0.01 to 2.0 MPa and at temperatures of −10° C. to 150° C. characterized in that a monolith catalyst is employed as the catalyst.

BRIEF DESCRIPTION OF DRAWING

The FIGURE depicts a preferred embodiment of the device of the present invention.

By carbonyl compounds, aliphatic, aromatic or heterocyclic aldehydes or ketones are to be understood, whereby several aldehyde and/or ketone groups can be present in the carbonyl compounds depending on the type of the molecule employed as the starting compound for ozonolysis and on the number of its double bonds. Carbonyl compounds which can be produced with the aid of the method as claimed in the invention, the corresponding compounds employed as starting materials and the production of corresponding peroxidic ozonolysis products are known, for example, from U.S. Pat. No. 4,607,126 and U.S. Pat. No. 4,769,464. The type of production of the peroxidic ozonolysis products is not critical for the method as claimed in the invention. Important is that the peroxidic ozonolysis products are at least partially dissolved in an organic diluting agent which is inert under the reaction conditions of hydrogenation. By an organic diluting agent, common diluting agents which are commonly employed for hydrogenolysis such as aliphatic or aromatic, if necessary chlorinated hydrocarbons such as pentane, hexane, cyclohexane, toluene, xylenes, methylene Preferably, peroxidic ozonolysis solutions in a low, aliphatic alcohol with 1 to 6 C atoms, especially preferably solutions of peroxidic ozonolysis products in an alcohol which was produced according to one of the methods described in U.S. Pat. No. 4,769,464 are employed in the method as claimed in the invention. Surprisingly however, the concentration of the peroxides in the solution is not of importance for the method as claimed in the invention. In general however, solutions of peroxidic ozonolysis products are produced in such a way that the peroxide concentration does not exceed 1.5 mole/l, since peroxides in relatively high concentrations tend towards explosive decomposition. Therefore, solutions with a peroxide concentration not exceeding 1.5 mole/l are preferable.

By a monolith catalyst, a catalyst consisting of a support coated with a catalyst basic substance is to be understood. Preferably, the support's surface is as large as possible, which can be obtained for example with a honeycombed or lamellar structure. The support is in one piece and can consist of the materials suitable for this purpose such as metal, glass, ceramic or plastic. A metal support is preferable, e.g. one consisting of steel or aluminum, since it has proven that these types can absorb the heat of the reaction and release it to the surrounding reaction medium uniformly. It was discovered that localized overheating can result in the reaction medium when non-conducting materials are employed as supports, meaning that the yield and purity of the reaction products may be interfered with.

By catalyst basic substance, basic substances commonly used in the reduction of organic peroxidic solutions are to be understood. Common basic substances are, for example, noble metals such as platinum, palladium, transitional metals such as nickel, cobalt, rhodium, their oxides, or mixtures of such metals or metal oxides. These metals can be partially poisoned by heavy metals such as lead or bismuth. Preferably, noble metals or mixtures of noble metals with transitional metals are employed as a catalyst basic substance in the method as claimed in the invention. In principle, the yields are independent of the amounts of basic substances employed in the method as claimed in the invention; however, it is advisable to start with 0.1 to 5.0 weight %, preferably 0.2 to 2.0 weight % basic substance in relation to the total amount of peroxidic solution in order to achieve a sufficient hydrogenation speed.

The production of such catalysts can be performed by means of a common coating process, e.g. by means of vapor deposition of the basic substance onto a support or impregnation of the support with the catalyst basic substance.

In order to conduct the method as claimed in the invention, the peroxidic ozonolysis products in the diluting agent employed are brought into contact with the monolith catalyst and with hydrogen. The monolith catalyst can be placed in the diluting agent containing the peroxidic ozonolysis products and hydrogen and stirred, or the diluting agent containing the ozonolysis product is continuously passed through the monolith catalyst together with hydrogen. Preferably, contact is continuous.

The reduction process, which generally proceeds exothermically, is conducted at temperatures of approximately −10° C. to 150° C., preferably at approximately 15° to 70° C., most preferably at approximately room temperature to 50° C. When doing so, the hydrogen is added as usual by being introduced or pressed on. In general, the hydrogen pressure amounts to 0.01 to 2.0 MPa, preferably 0.1 to 1.0 MPa. The respectively suitable hydrogen pressure and the respectively suitable temperature can be easily determined for the respective ozonolysis products by means of a preliminary test.

During the reduction process, the aldehydes, ketones or their hemiacetals, their acetals or their ketone acetals which correspond to the peroxidic ozonolysis products employed are formed. For working up the hydrogenated product solution is isolated from the catalyst in an uncomplicated fashion, e.g. by removing the catalyst support from the reaction mixture or by pumping the product solution out of the reaction container. Complex isolation of the catalyst suspension by means of filtering or centrifuging it off, as was previously necessary and which involves a fire hazard in that the catalyst suspension is brought into contact with atmospheric oxygen, is dispensed with. The hydrogenolysis product formed is isolated from the reaction mixture by removing the organic diluting agent and, if necessary, purified according to common methods such as crystallization, chromatography or distillation.

The present method may employ a device A for taking samples comprising the storage vessel V, the pump P, the hydrogen valve VE, the pressure gauge for hydrogen p, the monolithic catalyst F, the vessel G, the circulating pump K and the device for taking samples A being connected in sequence by means of lines for the reaction solution, whereby the concurrent feeding of the chemical compound to be subjected to hydrogenolysis and the hydrogen through the monolithic catalyst F and into the vessel G for collecting the reaction solution is ensured, and furthermore, whereby the possibility of the repeated feeding of the reaction solution from the collection vessel with the aid of the circulating pump through the monolithic catalyst is ensured.

In an especially preferred embodiment of the invention, a device as shown in the FIGURE is employed. In the FIGURE, V represents a storage vessel which contains the peroxidic ozonolysis products in the diluting agent employed. The peroxidic ozonolysis products can be directly fed into the storage vessel V from ozonolysis. The reaction solution is directed from V through the monolith catalyst F concurrently with hydrogen by means of a pump P and enters a vessel G, in which an arrangement T for controlling the temperature is mounted. With the aid of this arrangement, the temperature is maintained at room temperature to 60° C. The hydrogen pressure is adjusted to 0.1 to 0.3 MPa by means of a pressure gauge p and by means of a valve VE. As the reaction mixture is generally not fully hydrogenated after a single contact with the monolith catalyst F, it is then pumped out of the vessel G and through the monolith catalyst via the discharging device E1 by means of a circulating pump K until the peroxidic concentration in the reaction solution has sunk to the desired concentration as measured by an arrangement A. A monolith catalyst consisting of a metal tube containing honeycombs or lamellas which are coated with the catalyst basic substance is favorable. The metal tube can be constructed in such a way which allows it to be inserted directly into the reaction line, enabling the swift and uncomplicated exchange of the catalyst. Fixing the catalyst on a support excludes the possibility of sedimentation of the catalyst in the catalyst line.

In the event that distillable hydrogenation products are produced, the reaction solution is fed into a distillation unit D from the vessel G via the discharging device E2 after the completed reaction. The hydrogenation products are isolated in high yields and in high purity by distilling off the diluting agent employed. This type of device, which is suitable for the hydrogenolytic reduction of various chemical compounds which can be converted into uniform new products with the aid of a monolith catalyst and hydrogen, is new and also an object of the invention.

According to the method as claimed in the invention, peroxidic ozonolysis products are reduced to high yields of hydrogenation products with high purity directly after ozonolysis in an uncomplicated way, whereby it is not necessary to add a base and whereby dangerous and complex procedures for isolating the catalyst are avoided. The invention therefore represents an enrichment in the art.

EXAMPLE 1

To 187 g of maleic acid methyl ester (1.3 mole) in 1000 ml of methanol were added the equivalent amount of ozone by introducing a stream of 1000 l of oxygen containing 4 weight % ozone per hour at temperatures of −15° to −10° C. until the concentration of maleic acid methyl ester was less than 1% of the initial concentration.

The resulting peroxide solution was hydrogenated in the presence of a monolith catalyst consisting of a steel tube in which the lamellas coated with 7.2 g of platinum are located under a hydrogen pressure of 0.12 MPa. The absorbed hydrogen amounted to 28.6 normal liters or 98.2% of the theory. After the peroxide concentration decreased to <10 mmole/l, the reaction was stopped and the reaction solution was distilled at 55° C. and 25 torr after evaporating the methanol.

After doing so, 299.5 g of glyoxylic acid methyl ester hemiacetal, or 96% of the theory, with a purity of virtually 100% were obtained.

EXAMPLE 2

156 g of styrene in approximately 850 ml of methanol were treated with ozone as described in Example 1, whereby approximately 1 liter of a 1.5 molar peroxidic ozonolysis solution was obtained; this solution was treated with hydrogen in a device as depicted in the illustration at a temperature of 30° to 40° C. and a pressure of approximately 0.12 MPa in the presence of a metallic monolith catalyst coated with a Lindlar catalyst basic substance. The absorbed hydrogen amounted to 31.9 normal liters, or 94.9% of the theory. After completion of the reaction, the diluting agent was evaporated and the residue was vacuum-distilled. At a boiling point of 119° to 120° C./14 mm of Hg, 149.3 g of benzaldehyde, or approximately 94% of the theory in relation to the employed styrene, with a purity of virtually 100% were obtained.

EXAMPLES 3 and 4

These examples were conducted as described in Example 2 with the exception that 3. 177 g of 4-methyl styrene, whereby 32.4 normal liters of hydrogen, or 96.4% of the theory, were absorbed, 4. 121.5 g of isosafrole (3,4-methylenedioxy-(alpha-methyl)-styrene), whereby 15.8 normal liters of hydrogen, or 97.5% of the theory, were absorbed, were employed. When this was done at a boiling point of 3. 106° to 108° C./10 mm of Hg, 169 g of 4-methyl benzaldehyde, or 94% of the theory in relation to the 4-methyl styrene employed, 4. 106° to 107° C./4 mm of Hg, 140.6 g of heliotropine (3,4-methylenedioxybenzaldehyde), or approximately 94% of the theory in relation to the isosafrole employed, with a purity of virtually 100% were obtained.

EXAMPLE 5

This example was conducted as described in Example 2 with the exception that 223.5 g of 4-nitrostyrene were employed, whereby 31.8 normal liters of hydrogen, or 94.6% of the theory, were absorbed. After evaporating the diluting agent, the residue on evaporation was dissolved in hot water, and the solution was cooled in an ice bath. The precipitate was filtered off and dried. When this was done, 216 g of 4-nitrobenzaldehyde, or 96% of the theory in relation to the 4-nitrostyrene, with a melting point of 105° to 106° C. were obtained.

EXAMPLE 6

A 0.5 molar naphthalene solution in methanol was subjected to ozonolysis as described in Example 1. The 1 molar reaction solution of ortho-phthalic aldehyde ozonolysis products formed was directed continuously through a monolith catalyst at a hydrogen pressure of 0.12 MPa and at a temperature of 30° to 35° C. according to the illustration. When this was done, the peroxide concentration sank to a level lower than 10 mmole/l, and 94% of the theory of hydrogen was consumed. The methanol was evaporated from the product solution, which was drained off continuously, and the residue was dissolved in an amount of hot water sufficient to form a clear solution. When standing in the cold, a portion of the o-phthalic aldehyde formed crystallized out. The aqueous phase was extracted twice with diethyl ether; the already crystallized o-phthalic aldehyde was dissolved in the combined ether phase, and the organic solvent was evaporated.

When this was done, 88.2% of the theory of o-phthalic aldehyde with a purity of virtually 100% and a melting point of 54° C. were obtained.

EXAMPLE 7

This example was conducted as described in Example 6 with the exception that a monolith catalyst coated with palladium was employed. The absorbed hydrogen amounted to 97% of the theory; the yield of o-phthalic aldehyde was 90% of the theory and had a purity of virtually 100% and a melting point of 54° C.

EXAMPLES 8 and 9

These examples were conducted as described in Example 2 with the exception that 8. 210 g of dec-1-ene, whereby 32.4 normal liters of hydrogen, or 96.4% of the theory, were absorbed, 9. 172 g of 1,4-diacetoxy but-2-ene, whereby 21.8 normal liters of hydrogen, or 97.3% of the theory, were absorbed, were employed. When this was done at a boiling point of 8. 79° to 81° C./12 mm of Hg, 201 g of nonanal, or approximately 94% of the theory in relation to the dec-1-ene employed 9. 55° to 56° C./15 mm of Hg, 188 g of acetoxyacetaldehyde, or 92% of the theory in relation to the 1,4-diacetoxy but-2-ene employed, were obtained with a purity of virtually 100%.

EXAMPLE 10

1 l of a 1.5 molar methanol solution containing cyclooctadiene ozonolysis products, produced as described in Example 1, was reduced as described in Example 1. When this was done, hydrogen in the amount of 98% of the theory was absorbed. The product solution was acetalated for purposes of characterization, and the reaction mixture obtained was fractionated in a vacuum. When this was done, 1,1,4,4-tetramethoxybutane in the amount of 90.1% of the theory with a boiling point of 86° to 87° C. at 15 torr and a purity of virtually 100% was obtained.

EXAMPLE 11

This example was conducted as described in Example 6 with the exception that 123 g of cyclohexene were employed, whereby 30.5 normal liters of hydrogen, or 90.8% of the theory, were absorbed. The product solution was acetalated for purposes of characterization, and the reaction mixture obtained as a result was fractionated in a vacuum. When this was done, 275 g of 1,1,6,6-tetramethoxyhexane, or 89% of the theory in relation to the cyclohexene employed, with a boiling point of 111° C./20 mm of Hg and a purity of virtually 100% were obtained.

EXAMPLE 12

This example was conducted as described in Example 11 with the exception that 105 g of 2,5-dihydrofuran was employed, whereby 31.9 normal liters of hydrogen, or 94.9% of the theory, were absorbed. Oxime titration of the product solution yielded an aldehyde group content of the 3-oxaglutaraldehyde formed of 2.88 mole. This amounts to a yield of 96% of the theory in relation to the 2,5-dihydrofuran employed.

EXAMPLES 13 and 14

These examples were conducted as described in Example 2 with the exception that 13. 105 g of 2-vinylpyridine were employed, whereby 21.5 normal liters of hydrogen, or 96% of the theory, were absorbed, 14. 52.5 g of 4-vinylpyridine were employed, whereby 10.2 normal liters of hydrogen, or 91% of the theory, were absorbed.

When this was done at a boiling point of 13. 59° to 62° C./10 mm of Hg, 97.4 g of pyridine-2-aldehyde, or 91% of the theory in relation to the 2-vinylpyridine employed, 14. 70° to 72° C./10 mm of Hg, 48 g of pyridine-4-aldehyde, or approximately 90% of the theory in relation to the 4-vinylpyridine employed, with a purity of virtually 100% were obtained.

EXAMPLES 15 to 17

These examples were conducted as described in Example 2 with the exception that 15. 150 g of methylacrylic methacrylate were employed, whereby 32.2 normal liters of hydrogen, or 96% of the theory, were absorbed, 16. 171 g of methylacrylic ethyl acrylate were employed, whereby 31.9 normal liters of hydrogen, or 95% of the theory, were absorbed, 17. 192 g of ethylacrylic ethyl ester were employed, whereby 31.9 normal liters of hydrogen, or 95% of the theory, were absorbed.

When this was done at a boiling point of 15. 61° to 62° C./40 mm of Hg, 145.5 g of pyruvic methyl ester, or approximately 95% of the theory in relation to the methylacrylic methacrylate employed, 16. 78° to 80° C./15 mm of Hg, 164 g of pyruvic ethyl ester, or approximately 94% of the theory in relation to the methylacrylic ethyl acrylate employed, 17. 68° to 69° C./20 mm of Hg, 178 g of 2-oxo-ethyl butyrate, or approximately 92% of the theory in relation to the ethylacrylic ethyl ester employed, with a purity of virtually 100% were obtained.

What we claim is:

1. A method for the hydrogenolytic reduction of peroxidic ozonolysis products to the corresponding carbonyl compounds in an organic diluting agent which is inert under the reaction conditions in the presence of a catalyst at a hydrogen pressure of 0.01 to 2.0 MPa and at temperatures of −10° to 150° C. comprising employing a monolith catalyst as catalyst.

2. The method as claimed in claim 1 comprising the monolith catalyst consisting of a catalyst support which is coated with a noble metal.

3. The method as claimed in claim 1 comprising the catalyst support consisting of a metal.

4. The method as claimed in claim 1 comprising employing an alcohol with 1 to 6 C atoms as an inert, organic diluting agent.

5. The method as claimed in claim 1 comprising maintaining a hydrogen pressure of 0.1 to 1.0 MPa.

6. The method as claimed in claim 1 comprising maintaining a temperature of 15° to 70° C.

7. A method as claimed in claim 1 comprising employing a device for the hydrogenolysis of chemical compounds with hydrogen which contains a storage vessel V for the chemical compound to be subjected to hydrogenolysis, a pump P for feeding in the chemical compound, an arrangement VE for introducing the hydrogen and a pressure gauge p for measuring the hydrogen pressure, a container F with a monolith catalyst, a vessel G for collecting the reaction solution which contains an arrangement T for controlling the temperature and arrangements E1 and E2 for withdrawing the product solution, a circulating pump K for transporting the reaction solution, and a device A for taking samples comprising the storage vessel V, the pump P, the hydrogen valve VE, the pressure gauge for hydrogen p, the monolith catalyst F, the vessel G, the circulating pump K and the device for taking samples A being connected in sequence by means of lines for the reaction solution, whereby the concurrent feeding of the chemical compound to be subjected to hydrogenolysis and the hydrogen through the monolith catalyst F and into the vessel G for collecting the reaction solution is ensured, and furthermore whereby the possibility of the repeated feeding of the reaction solution from the collection vessel with the aid of the circulating pump through the monolith catalyst is ensured.

* * * * *